(12) United States Patent
Guillama et al.

(10) Patent No.: US 12,249,428 B2
(45) Date of Patent: Mar. 11, 2025

(54) WELLNESS MONITORING BY MEASUREMENT OF INCIDENTAL ROUTINE

(71) Applicant: The Quantum Group, Inc., Lake Worth, FL (US)

(72) Inventors: Noel J. Guillama, Wellington, FL (US); Chester A. Heath, Boca Raton, FL (US)

(73) Assignee: The Quantum Group, Inc., Lake Worth, FL (US)

( * ) Notice: Subject to any disclaimer, the term of this patent is extended or adjusted under 35 U.S.C. 154(b) by 0 days.

(21) Appl. No.: 18/657,608

(22) Filed: May 7, 2024

(65) Prior Publication Data

US 2024/0290500 A1 Aug. 29, 2024

Related U.S. Application Data

(63) Continuation of application No. 16/169,592, filed on Oct. 24, 2018, now Pat. No. 12,009,101.

(60) Provisional application No. 62/576,160, filed on Oct. 24, 2017.

(51) Int. Cl.
| | | |
|---|---|---|
| *G16H 50/30* | (2018.01) |
| *G06V 40/20* | (2022.01) |
| *G16H 10/60* | (2018.01) |
| *G16H 20/70* | (2018.01) |
| *G16H 40/67* | (2018.01) |
| *H04L 67/12* | (2022.01) |
| *H04L 67/50* | (2022.01) |
| *G06V 40/10* | (2022.01) |
| *G06V 40/18* | (2022.01) |

(52) U.S. Cl.
CPC ............. *G16H 50/30* (2018.01); *G06V 40/20* (2022.01); *G06V 40/25* (2022.01); *G16H 10/60* (2018.01); *H04L 67/12* (2013.01); *H04L 67/535* (2022.05); *G06V 40/15* (2022.01); *G06V 40/193* (2022.01)

(58) Field of Classification Search
None
See application file for complete search history.

(56) References Cited

U.S. PATENT DOCUMENTS

| | | | |
|---|---|---|---|
| 7,020,508 B2 * | 3/2006 | Stivoric | A61B 5/0537 |
| 2005/0131736 A1 * | 6/2005 | Nelson | G16H 40/67 |
| | | | 705/2 |
| 2006/0084847 A1 | 4/2006 | Reed | |
| 2008/0033252 A1 | 2/2008 | Estrella | |

* cited by examiner

*Primary Examiner* — Hung Q Dang
(74) *Attorney, Agent, or Firm* — Nixon Peabody LLP

(57) ABSTRACT

The present disclosure provides for the automatic measurement of measurable incidental routine parameters (MIRP). MIRP can include every movement of the body and a user's routine. This data can be incorporated into an accurate and comprehensive evaluation of a user's routine. The present disclosure functions by identifying normalcy for an individual in the consistency of habitual movement and behavior. This normalcy can become an indicator of wellness. Therefore, the present disclosure provides systems or methods which can objectively analyze a user's behavior to provide holistic predictors and analysis of a user's health.

20 Claims, 12 Drawing Sheets

| 310 Fred | Time | 320 Gregory | Time |
|---|---|---|---|
| | $t_0$ = 1 am | | $t_0$ = 11:30 pm |
| | $t_1$ = 8:00 am | | $t_1$ = 7:00 am |
| | $t_2$ = 8:01 am | | $t_2$ = 7:01 |
| | $t_3$ = 8:02 am | | $t_3$ = 7:11 AM |
| | $t_4$ = 8:07 am | | $t_4$ = 7:15 AM |
| | $t_5$ = 8:17 am | | $t_5$ = 7:40 am |
| | $t_6$ = 8:20 am | | $t_6$ = 7:54 am |
| | $t_7$ = 8:21 am | | $t_7$ = 8:01 am |
| | $t_8$ = 8:28 am | | $t_8$ = 8:10 am |
| | $t_9$ = 8:35 am | | $t_9$ = 8:20 am |
| | $t_{10}$ = 8:40 am | | $t_{10}$ = 8:30 am |
| | $t_{11}$ = 8:45 am | | $t_{11}$ = 8:45 |

| Event | Day 1 | Day 2 | Day 3 | Day 4 | Day 5 | Day 6 | Day 7 | |
|---|---|---|---|---|---|---|---|---|
| 1 | 01:00 | 01:01 | 12:59 | 01:15 | 02:00 | 03:03 | 12:00 |  |
| 2 | 08:00 | 08:00 | 08:00 | 08:01 | 07:58 | 09:59 | 11:11 |  |
| 3 | 08:01 | 08:01 | 08:01 | 08:01 | 08:01 | 10:00 | 11:12 |  |
| 4 | 08:02 | 08:02 | 08:03 | 08:02 | 08:03 | 10:02 | 11:15 |  |
| 5 | 08:07 | 08:06 | 08:08 | 08:07 | 08:06 | 10:10 | 11:17 |  |
| 6 | 08:17 | 08:16 | 08:18 | 08:17 | 08:16 | --:-- | --:-- |  |
| 7 | 08:20 | 08:20 | 08:20 | 08:20 | 08:20 | 10:20 | --:-- |  |
| 8 | 08:21 | 08:21 | 08:21 | 08:21 | 08:21 | 10:21 | 11:21 |  |
| 9 | 08:28 | 08:28 | 08:28 | 08:28 | 08:28 | 11:21 | 11:26 |  |
| 10 | 08:35 | 08:35 | 08:35 | 08:35 | 08:35 | 11:36 | 11:37 |  |
| 11 | 08:40 | 08:40 | 08:41 | 08:39 | 08:40 | 11:41 | 11:40 |  |
| 12 | 08:45 | 08:46 | 08:43 | 08:44 | 08:46 | 11:47 | 11:59 |  |

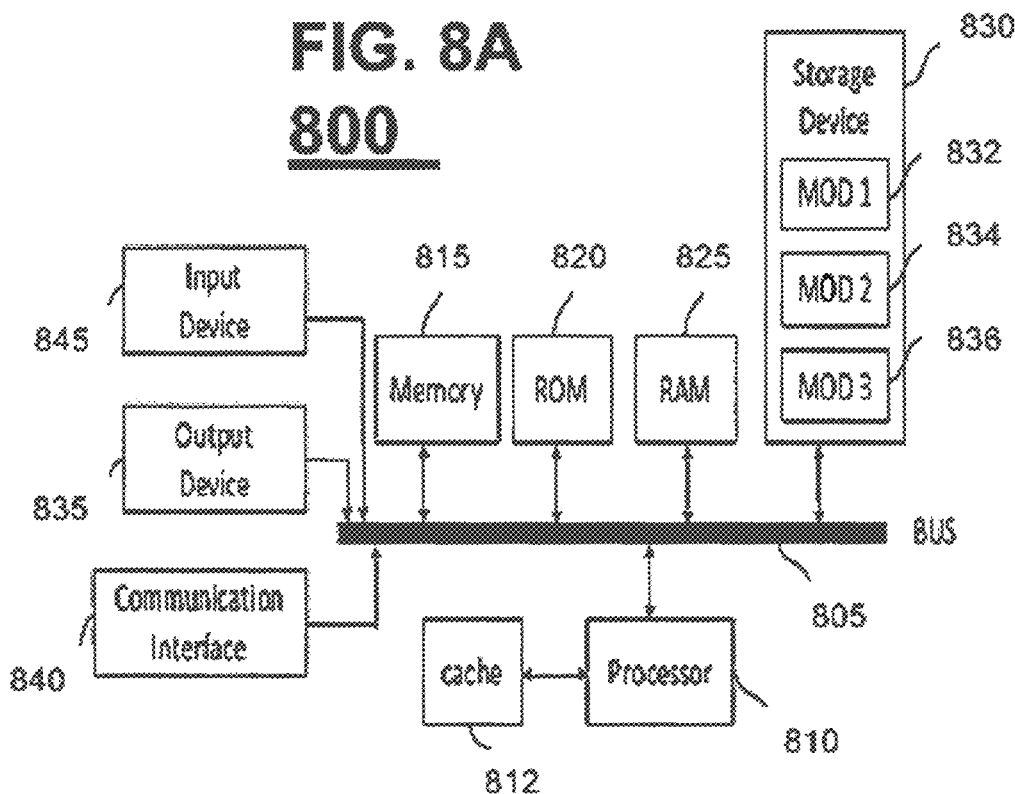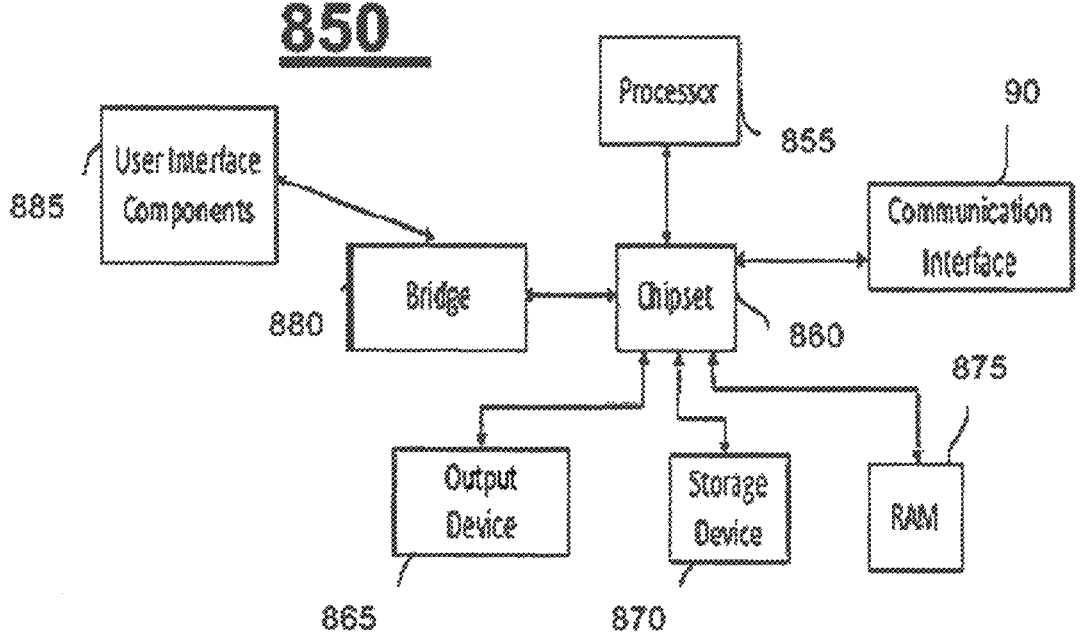

WELLNESS MONITORING BY MEASUREMENT OF INCIDENTAL ROUTINE

CROSS REFERENCE TO RELATED APPLICATIONS

This application is a continuation of U.S. application Ser. No. 16/169,592, filed Oct. 24, 2018, now allowed, which claims the benefit of and priority to U.S. Provisional Application No. 62/576,160, filed Oct. 24, 2017, each of which is hereby incorporated by reference herein in its entirety.

FIELD OF THE INVENTION

The present disclosure relates to systems and methods for measuring wellness according to relationships between routine events.

BACKGROUND

Conventional methods of tracking human wellness involve isolated sensors or technologies which evaluate one part of a user's actions. For example, wearable technologies can measure distance moved or heart rates. Such technologies give limited insight into a person's wellness and do not allow holistic predictors of how an individual is doing on a daily basis. Some conventional methods and systems try to help analyze human wellness by providing a user with a user-operated device to call for support. However, users can be incapacitated and unable to operate the device to call support. In other cases, users may choose not to call for support based on an incorrect, subjective view of their personal health. In such cases, the users may become incapacitated later and unable to request assistance, rendering such conventional methods/systems ineffective. Therefore, conventional systems and methods fail to provide adequate, objective analysis and predictions of a user's wellness on a holistic basis.

Similar to tracking human wellness, conventional systems and methods fail to adequately track wellness of computer systems. Some conventional methods have attempted to measure and predict computer system diagnostics and performance. Some methods measure computer system health by looking at indicators of system responsiveness, connectivity, and freedom from spontaneous errors and delays. Computer systems and various technologies are so ingrained in society that a user can consider the health of his technology as integral as the user's personal health. However, there are limited, comprehensive methods which can monitor computer system procedures to detect whether the computer system is functioning as expected. For example, if there are delays during start-up or shut-down, computer systems do not log the delays; rather computer systems simply record whether each task is completed. Therefore, current systems and methods do not identify when some system process is not as timely as expected and can fail to identify early symptoms of system failure. Furthermore, most computer systems are not set-up to handle such amounts of data measuring all system diagnostics and timings due to the complexity and size of the data required.

SUMMARY

The present disclosure provides systems and methods for wellness monitoring. An exemplary method can include receiving a plurality of event data from a plurality of sensors. The plurality of data can include data on a plurality of events. Data for each event can indicate whether a particular event occurred and the time that the particular event occurred. The method can provide for analyzing the timing and completion of the plurality of events to determine (1) correlations between different events and (2) appropriate timing of the events. The method can then provide for determining whether any of the plurality of events failed to pass a wellness metric. The wellness metric can provide predictions about whether and when a particular event should have occurred. The wellness metric can include expected ranges of timing. In some examples, the method can provide for sending a notification that an event has not occurred that should have occurred or that the event did not occur during a predicted timeframe.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIGS. 3A-3B show an exemplary sets of routine data captured for two individuals, according to an embodiment of the present disclosure.

FIGS. 8A-8B show exemplary computer systems, according to an embodiment of the present disclosure.

DETAILED DESCRIPTION

Figure 1A:
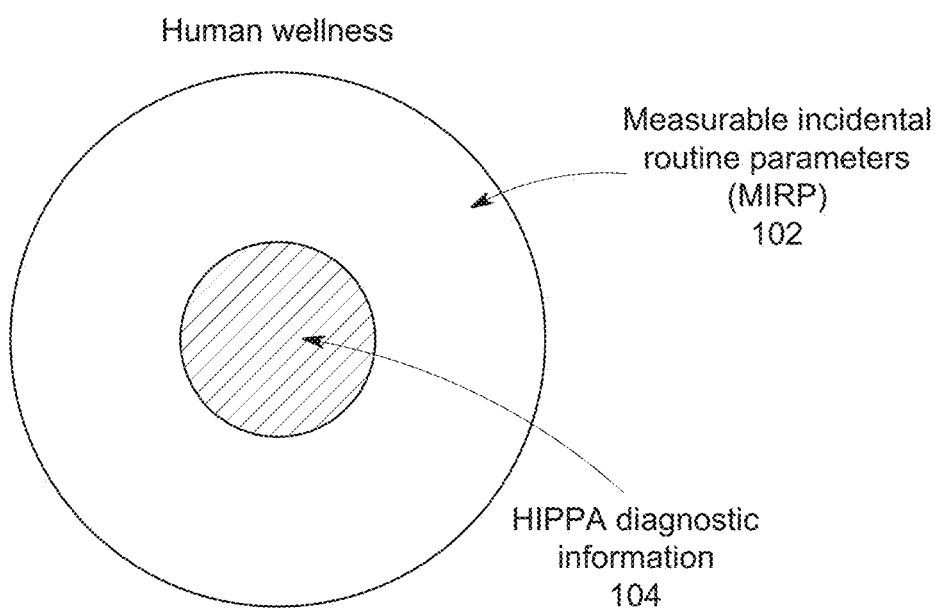
FIG. 1A shows an exemplary schematic of data collected by medical health professionals versus data available to predict human wellness.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure is directed to systems and methods for wellness monitoring. An exemplary system can include a plurality of sensors. The plurality of sensors can be configured to detect event data. The event data can include data for a plurality of events indicating whether a particular event in the plurality of events has occurred and timing of the event particular event. The plurality of sensors can be configured to send the event data to a first computing device. The computing device can include a memory containing machine readable medium. The machine readable medium can include machine executable code having stored thereon instructions for performing a series of steps. The steps can include first receiving the plurality of event data. The steps can then provide for analyzing the plurality of event data to detect routine timing and routine correlations between different events in the plurality of events. The steps can then provide for detecting whether a particular event occurred in a non-routine manner, based on the routine timing and routine correlations.

The present disclosure provides for the automatic measurement of measurable incidental routine parameters (MIRP). MIRP can include every movement of the body and a user's routine. This data can be incorporated into an accurate and comprehensive evaluation of a user's routine. The present disclosure functions by identifying normalcy for an individual in the consistency of habitual movement and behavior. This normalcy can become an indicator of wellness. Therefore, the present disclosure provides systems or methods which can objectively analyze a user's behavior to provide holistic predictors and analysis of a user's health.

FIG. 1A shows an exemplary schematic of data collected by medical health professionals versus data available to predict human wellness. FIG. 1A shows how HIPPA diagnostic information 104 comprises a small portion of the variables which predict and show human wellness. Measurable incidental routine parameters (MIRP) 102 comprise the remainder of variables showing human wellness. However, conventional systems only rely on diagnostic information 104 to determine human wellness. Therefore, the present disclosure discusses systems and methods to analyze MIRP 102 to predict human wellness (discussed later with respect to FIGS. 2-7).

Measurable medical parameters 104 involve parameters like blood oxygen level, AIC (sugar saturation in blood hemoglobin), concentrations of white blood cells, hormone levels, or even genetic makeup. Importantly, these parameters 104 are private to each individual, and HIPPA laws prevent dissemination to other than authorized medical specialists. HIPPA diagnostic information 104 therefore captures a small amount of the data which can be relevant to a user's well-being.

Figure 3A:
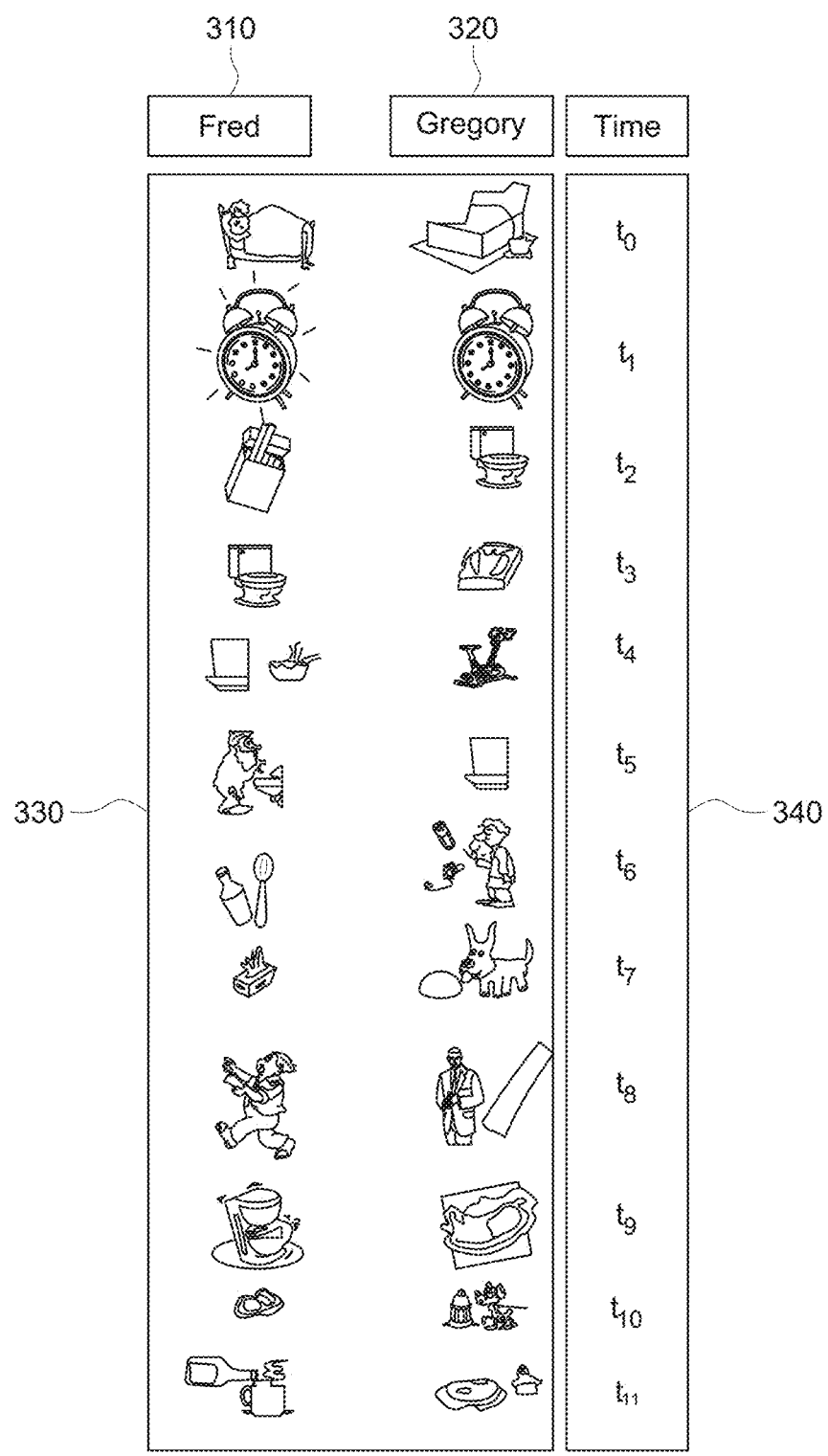
Figure 3C:
FIG. 3C shows exemplary sets of routine data captured over a period of time, according to an embodiment of the present disclosure.
Figure 3C:
Figure 3C:
Figure 3C:
Figure 3C:
Figure 3C:
Figure 3C:
Figure 3C:
Figure 3C:
Figure 3C:
Figure 3C:
Figure 3C:

By contrast, the measurable incidental parameters (MIRP) 102 can include elements of a user's routine, completion of the element, and timing of the completion (discussed further with regards to FIGS. 3A-3C). MIRP 102 can be disclosed to anyone, or any chosen machine. Additionally, MIRP 102 can be more indicative of an individual's well-being. Therefore, an exemplary system or method, according to the present disclosure, which relies on unprotected data can be highly efficient for a user who does not have to worry about legal constraints on the release of the data. MIRP 102 can be as telling of wellness as are measurable medical parameters 104.

An exemplary system, according to the present disclosure, can provide for the storage of both sets of data 102 and 104 in a HIPPA compliant Electronic Healthcare Records (EHR) system where they can then be collectively analyzed against each other in a protected environment.

Therefore, the present disclosure provides systems and methods ideal for the wellness monitoring of those people who live alone. People who live alone now make up 27% of the population and that number is expected to grow as high as 37%, as baby boomers qualify for assisted living, home visitation and nursing homes.

Figure 1B:
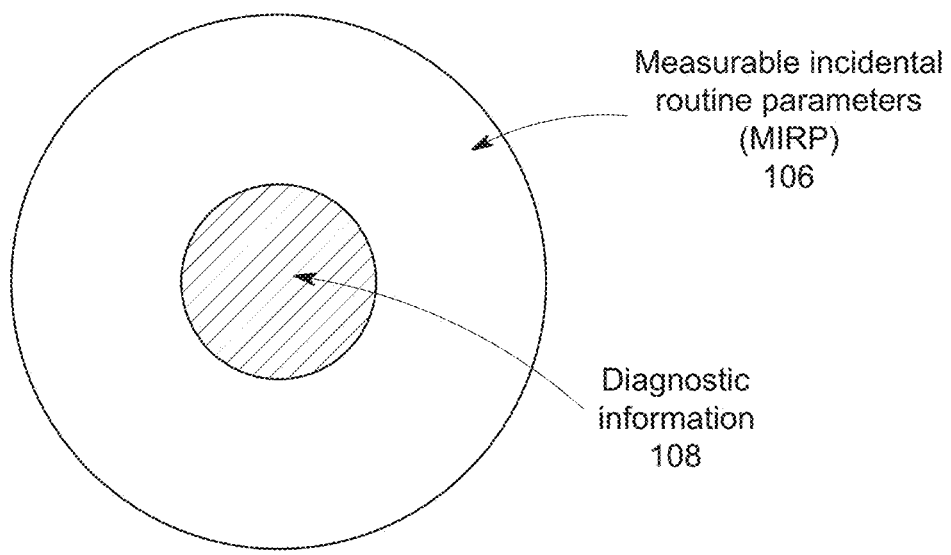
FIG. 1B shows exemplary schematic of data collected by computer system diagnostics versus data available to predict computer system functionality.

FIG. 1B shows exemplary schematic of data collected by computer system diagnostics versus data available to predict computer system functionality. FIG. 1B shows how diagnostic information 108 comprises a small portion of the variables which predict and show computer system functionality. Measurable incidental routine parameters (MIRP) 106 comprise the remainder of variables showing computer system functionality. However, conventional systems and methods only rely on diagnostic information 108 to determine computer system functionality. Therefore, the present disclosure discusses systems and methods to analyze MIRP 106 to predict computer system functionality (discussed later with respect to FIGS. 2-7).

Diagnostics 108 in a computer are distinct routine actions. MIRP 106 in computers can be the time to complete specific sections of the Power On Self Test (POST), the time to test memory, or enumerate I/O devices, or configure the hardware adapters. MIRP 106 can include the time to load drivers, the time to present a first image to the screen, the time to read a sector on the disk, the number of retries required to read that sector. POST does not typically record the timing of all the MIRP events in the startup of a computer, it records diagnostic information 108 as to whether they occurred successfully, or not.

If all MIRP 106 were recorded and compared on each startup—the complexity and speed would be beyond most computers. Indeed, a second intelligence, inside the system, to monitor all this detail could easily be required and would have to begin its monitoring long before any application was loaded; it would have to begin at power on.

MIRP 106 can tell if something abnormal was disrupting the initial rhythm originally recorded when a computer system was first configured and enabled. Therefore, analysis of MIRP 106, according to an embodiment of the present disclosure (such as discussed with respect to FIGS. 5A-5B)

can identify when a computer system is performing poorly and can identify where to focus diagnostics.

Humans, computers, and animals all have MIRP 102. Therefore, although the present disclosure focuses on MIRP as it applies to humans, a person skilled in the art can readily understand how to apply the present disclosure for routine parameters of computers and animals. Some examples are discussed later, herein.

Figure 2:
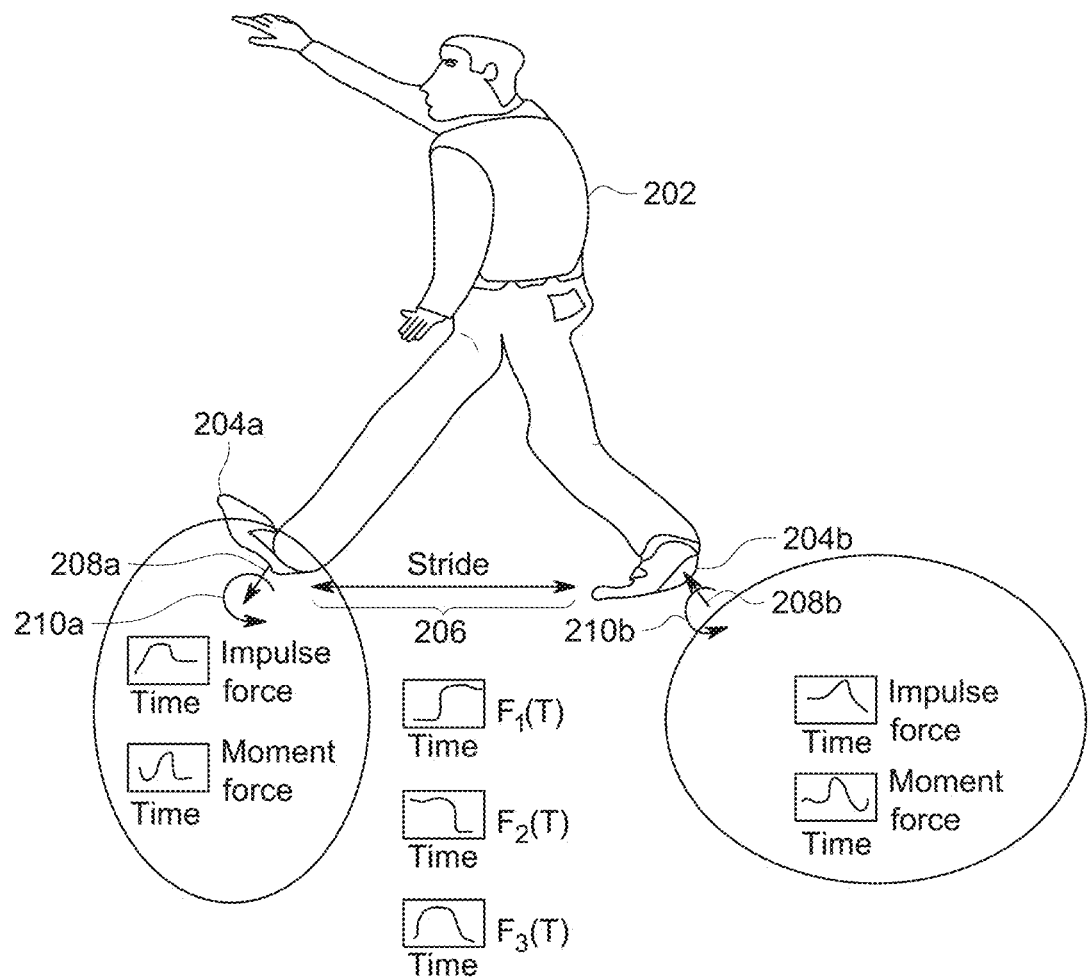
FIG. 2 shows a schematic of an exemplary system for collecting stride data, according to an embodiment of the present disclosure.

FIG. 2 shows a schematic of an exemplary system 200 for collecting stride data, according to an embodiment of the present disclosure. An exemplary system 200 can include a user 202; a first shoe 204*a*; a second shoe 204*b*; a measurement of stride 206; measurements of impulse force 208*a* and 208*b*; and measurements of moment force 210*a* and 210*b*. The user 202 can have a plurality of sensors (not pictured) on him to detect his movement. For example, his shoes 204*a* and 204*b* can have sensors configured to measure a length of his stride 206, impulse force 208*a* and 208*b* of his steps for each foot, and moment force 210*a* and 210*b* of his steps for each foot. This data can be used to determine whether the user 202 is walking in a different manner than his history, whether he is limping or favoring a foot, whether he is moving slower or faster, and many other variables, all which can be used as indicators of the user's 202 wellness.

Fundamentally, each data point in a routine can include a time stamp, numeric value and a meaning. The meaning can be an eye blink, upright orientation and stature, or step force. The data points can be associated with each other. For example, the measurement of gait or spring when walking can involve a series of points from a plurality of sensors in a shoe, in slippers, in socks, or embedded within the body. Embedded sensors can also detect via Electromyogram (EMG) the command to the muscles and sense muscle responsiveness, positioning and forces in the foot. All of these measurements have consistency for an individual that can change with time. These measurements can be a unique signature of that individual, which is indicative of the relative daily wellness of the person. These measurements can be recognizable externally, for example, by cameras that can infer or verify these parameters to determine the mass and distribution of mass within that individual's body.

Analysis of this data collected from sensors can infer the condition of muscles, tendons, and joints involved in positioning the pedal extremities. Comparison of forces between the two feet can detect skeletal issues. This detection can come long before the individual notices any abnormality, because the individual can change his perception of what he considers normalcy over time as his body slowly changes. However, the present disclosure can provide specific relationships between collected data points to provide wellness analysis.

System 200 provides one example of a sensor system. The present disclosure conceives of sensor systems in any aspect of a user's 202 routine. Sensors can be any a device, module, or subsystem whose purpose is to detect events or changes in its environment and send the information to other electronics. For example, a sensor system in a house can include a variety of household objects connected to an online data source. The household objects can include a doorbell with video, a bed, an alarm clock, a toilet, a mirror, a coffee pot, a refrigerator, and slippers. These physical instrumentalities can be intelligent in that they map and record a user's movement through his household. For example, a user can wake up at 7:42, push the off button on the alarm clock 15 seconds later, operate the commode until 7:44, then the shower till 7:55, look in the mirror at 8:05 to shave and see a reversed image. A camera can produce this image in the mirror, and can also test the user's blink rate, blink duration, and even give a micro flash to measure responsiveness.

A user can then slip into slippers (which measure balance, gait, weight, and the spring in a user's step), turn on the coffee pot at 8:06, put in a cup at 8:07, press brew 15 seconds later, open the refrigerator for cream at 8:08, then walk out to the door to retrieve the paper at 8:10, and sit down at the table at 8:12. These 30 minutes are exemplary of a morning routine whose events follow essentially the same sequence for a given individual most every work day.

An exemplary sensor system can detect when routine actions don't occur, or occur inconsistently. These changes can be an indication of something seriously abnormal. And in those situations, a system according to an embodiment of the present disclosure can send an alert to the user. An exemplary alert can ask: "Are You OK?" or stimulate investigation by a caregiver.

Exemplary sensors can detect when, a person, unconscious on the floor, does not trigger the sensors in their shoes, has an unnatural position to a camera observing the room, and stops the user's normal routine. Therefore, the present disclosure provides better prediction than conventional methods which rely on just wellness information and vitals which appear completely normal and do not capture these breaks from routine. And, an unconscious person can be unable to press an amulet and can have slowly fainted in an action not otherwise discernible from bending or sitting down to tie a shoe. It is the absence of normal routine that signals the abnormal situation—not simple telemetry of their vitals.

Much of the data collected by the sensors can comprise data that is largely undetectable to an observing human, such as blink frequency and length of an eye blink. Other detectable elements can include stress analysis of an individual's voice, general weight gain or loss, impact to movement or inertia, externally measured temperature, completeness and speed of routine bodily functions. Additionally, the data captured by the sensors can provide a complex monitoring framework that reviews current and past data to determine whether detected sensor data falls within a user's routine. An exemplary system can continuously and automatically receive sensor data and update a memory on occurrences and timings of a plurality of events. In order for the data collected by the sensors to be useful to a user, the data analysis must be a constant monitoring system with instant feedback. The instant feedback provided by the present disclosure allows a user (or a caregiver of the user) to be notified in a timely manner.

An exemplary system can prod a user along when the user is potentially in danger of being late for certain events. In some examples, an exemplary system can determine that a user's responses are impaired, or otherwise degraded, and then prevent the user from completing certain tasks that pose a danger to the user or others. For example, the exemplary system can require the user to surrender manual operation of an automobile to self-driving mode.

In some examples of the present disclosure, sensors can be embedded in the human body, can be wearables attached to or worn by the user, or can be separate sensors configured to observe the user. Typical data of a user's routine is not used to predict or monitor anything about the user. Such data is discarded and never analyzed by conventional methods. However, the present disclosure can be an automated EHR system designed specifically to collect and analyze MIRP data collected by sensors.

The present disclosure can provide significant advantages to sports medicine and training. For example, with video observation of a user and data collected by a plurality of sensors, one can learn to perfect a skill more quickly and accurately than without an embodiment of the present disclosure. Analysis in the development of proper movement can be beneficial to handicapped or rehabilitation individuals, who are recovering from injury or obviating birth defects.

Moore's law can explain how sensor systems, according to the present disclosure, can be sufficiently complex and intelligent to handle the vast amounts of data as conceived by the present disclosure. Moore's law explains that silicon logic becomes denser, more complex, and faster on regular intervals. As a first corollary, logic and memory are predicted to use less power and become smaller, cheaper, and closer to the edge of connectivity. As a second corollary, this allows software to become more complex. As a third corollary, mobile systems specifically benefit through the general connectivity of all devices as new application areas will spring up spontaneously. While silicon logic and memory become highly competent and the price of such memory becomes cheaper, a greater number of everyday items can be intelligent and inter-connected, providing their data for analysis.

Moore's law predicts that the interconnectivity of the modern world and the capabilities of silicon logic will double approximately every two years, quadruple by five years, octuple in a decade, and double again a few years after that. Over time, the limit of performance and complexity of intelligent systems is unlimited, and the manufacturing cost will no longer be a major factor. Therefore, systems can handle the vast amount of data accumulated by a plurality of sensors.

FIGS. 3A-3B show an exemplary sets of routine data captured for two individuals, according to an embodiment of the present disclosure. FIG. 3A can include a first user 310; a second user 320; a plurality of events 330; and a plurality of times 340 for each event 330. The users 310 and 320, events 330, and timings 340, can be as described with respect to FIG. 2. FIG. 3B shows a first user, Fred, 310, with a specific routine 315, with a specific schedule 345. FIG. 3B also shows a second user, Gregory, 320, with his own routine 350 and schedule 355.

FIGS. 3A-3B depict comparable routines between two single individuals Fred Flynstein (F) 310 and Gregory Grede (G) 320 who have very dissimilar lives and habits, but they are typically consistent in their morning routines 315 and 350. For example, Gregory 320 can work as a Hedge Fund Manager and Fred 310 can work on the subway. FIG. 3A depicts their exemplary schedules in the abstract. FIG. 3B demonstrates an exemplary timeline as compared between the two.

For example, Fred 310 goes to bed shortly after the bars close at 1 am and his alarm goes off at 6 am; he is due at work to drive the subway at 9 am. His first event is a grab for a cigarette at 8:01, almost as his eyes open. At 8:02 he continues the smoke as he visits nature and ends the cigarette as he enters the shower at 8:07 and then shaves at 8:17. He brushes his teeth at 8:20 and begins his first hack at 8:21. Fred 310 rushes to dress at 8:28 and brews a cup of coffee at 8:35 that washes down his pills at 8:40. At 8:45 he adds flavor to his coffee, and is out the door.

Gregory 320 schedules his bedtime against the lunch breaks of the Tokyo and Shanghai stock exchanges at 11:30 pm and is awake at 7 am as the London exchanges goes to lunch. At 7:01, he multi-tasks as he checks his bathroom laptop against the overseas progress. At 7:11, he measures his weight and begins his 25-minute exercise (thoroughly monitored according to an exemplary sensor system, according to an embodiment of the present disclosure) regimen at 7:15. At 7:50, he is showering. At 7:54, he grooming for the day and feeds his Scottish Terrier at 8:01. Over the next 9 minutes, he converses with the dog, as it enjoys its meal and he dresses with clothes from the closet—where hangers can count the usage and placement of garments. At 8:20, he enjoys a cup of Chinese tea and walks the dog at 8:30. By 8:45, he is back for breakfast and afterward he is headed to work by way of the subway. Both Fred 310 and Gregory 320 are locked into a routine. Indeed, such that Fred 310, working on the subway, unknowingly drives Gregory 320 to work every morning.

Fred 310 and Gregory 320 each live alone, as do more than a quarter of the adults in the US. Each individual's unique routine has consistency, because they are bounded by the times that they awaken and the times they are due to work and the duties that they must perform in between. The first sign that anything was amiss with their wellness would be a disruption in their routines 315 and 350. The routines 315 and 350 can be detected by sensors in the bed, the alarm clock, and the commode. For example, infrared cameras can detect the first cigarette; the network can detect the activities of the laptop. The plumbing of the showers and sinks can detect their operation and even regulate temperature. The toothbrush, floss package, and electric razor can be wired by Wi-Fi and are even monitored for when they need attention. Even bottles can report on the state of its contents and use. The Scottish Terrier can be wired by a RFID chip that identifies him and also monitors his movement. For example, Scottish Terriers can be very prone to hip problems that will alter the stoic dog's gait well before there is any outward symptom of pain. The dogs bowl and the cupboard and refrigerator can all indicate when more dog food is required. Similarly, the residence can maintain a perpetual inventory ordering system for all commodities in the home including the shaving cream, toothpaste, aspirin, coffee, eggs, and sausage.

A system, according to the present disclosure, can compare the elements within multiple routines 315 and 350 to determine correlations. There can be many very complex correlations and sequences that exceed the capacity of the human mind to analyze. FIG. 3C shows exemplary sets of routine data captured over a period of time, according to an embodiment of the present disclosure.

Each routine 315 and 350 can be analyzed for correlation between individual events and their timings within the routine or as between routines. Trends and correlations can be noted with anomalies screened for frequency. For example, each human has about 30,000 days in a lifetime. Individual routines can develop and evolve over long periods of time and through an affinity association with other individuals. Therefore, the continuous monitoring of the present disclosure can provide the holistic, learning approach which can provide accurate information on a user's wellness.

FIG. 3C shows an exemplary chart of a collection of F (tn) with time intervals across the top in days and (am) time of events for Fred's 12-step morning routine. FIG. 3C shows, for example that Fred is out late and sleeps in on weekends, and a trend analysis (discussed further with respect to FIGS. 4A-4c) would allow for that. Fred doesn't shave on weekends and sometimes forgets to brush his teeth.

Therefore, FIGS. 3A-3C provide exemplary sets of data which can belong to the user and cannot be released without his permission. An exemplary sensor system can provide the user with an indication of where the user was on a certain night and a prediction of where the user might be on a future night.

Figure 4A:
FIGS. 4A-4C show exemplary formulas to characterize sample data, according to an embodiment of the present disclosure.
Figure 4B:
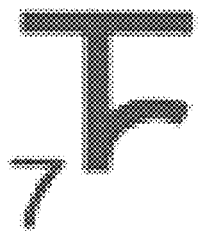
Figure 4C:
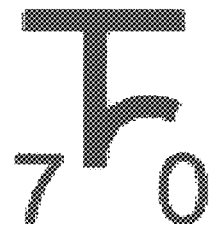

FIGS. 4A-4C show exemplary formulas to characterize sample data, according to an embodiment of the present disclosure.

FIG. 4A can define an operator "Trend". Trend is the collection over time, at given intervals. For example, FIG. 3C can be represented by FIG. 4B to show the trend interval is 7. Therefore, in this example, each day of the week correlates.

For example, f(t)→F(T) can be a collection of strides at discrete times and F(T)={(F(T0)), (F(T1)), (F(T2)), ..., (F(T6))}, (F(T7)), (F(T8)), (F(T9)), ..., (F(T13))}, ... can follow the 7-day interval example.

FIG. 4C shows how the Trend can be the vertical slice; where the Trend identifies row 1, col 1; row 2, col 1; row 3, col 1; row n, col 1.

The mean and standard deviation of the Trend can be formed to become the base for comparison of future measurements. The mean and standard deviation provide an initial estimate of "normalcy" for the interval.

After determining a trend for each event, the present disclosure can then provide for comparing subsequent measurements to the (continuously updated) mean and standard deviation for the metric. For example, the trend of metric F can then be thereby auto-correlated at a 1-week interval. For example, when a preset number of multiple statistics are outside the nominal 2 standard deviation range, then a fault can be declared.

A deviation from normalcy is when the timing and/or sequence is off or the event does not occur. These examples are discontinuous functions of events, which are typically designated by a number or title. The event and timing, and therefore sequence, are compared in a similar manner to the trend-they are compared to an on-going tally of normal MIRP. Limits can be defined as to the importance of the event. For example, failure to awaken in response to the alarm clock is considered more serious than not eating breakfast, or not weighing oneself after routine exercise. However, a trend of consistently not completing the monitored exercise regimen, or completing it with inadequate performance, can designate a serious health problem.

Figure 5A:
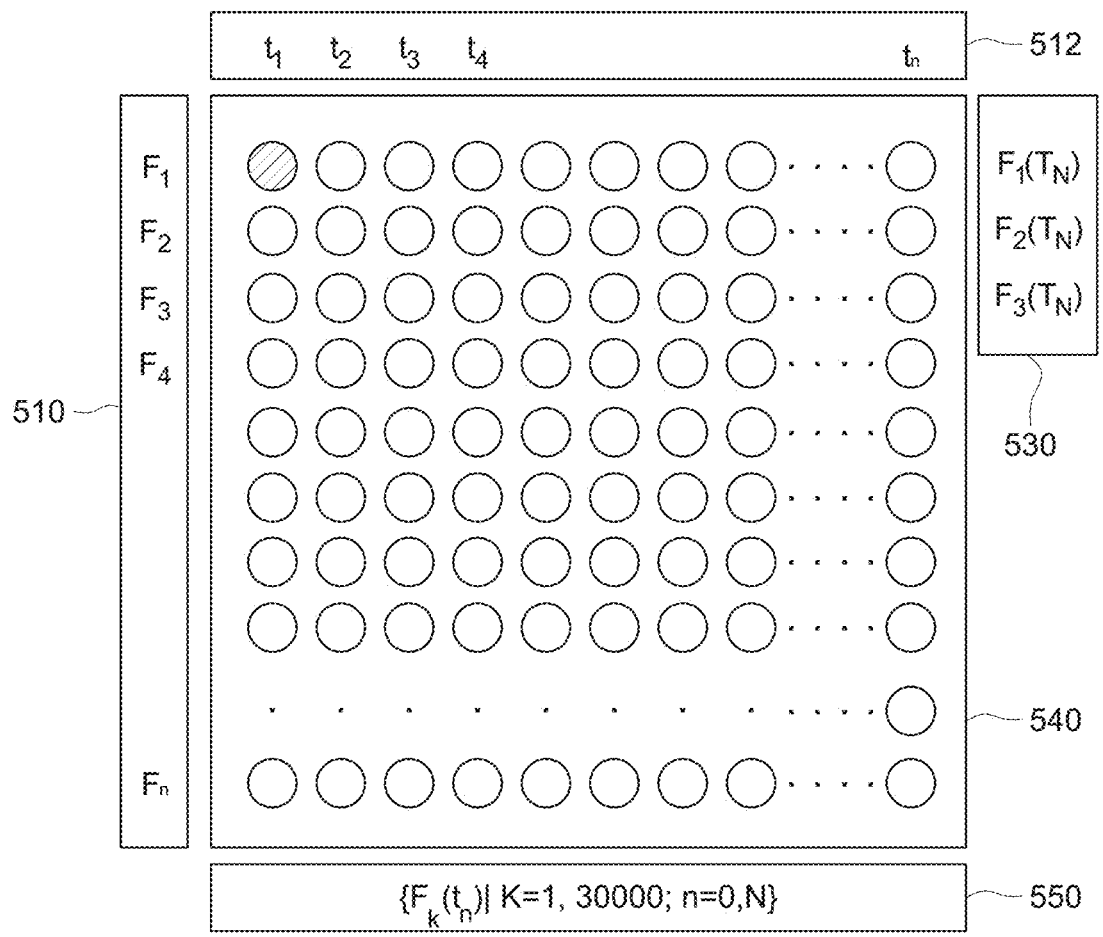
FIG. 5A shows an exemplary set of data, according to an embodiment of the present disclosure.

FIG. 5A shows an exemplary set of data, according to an embodiment of the present disclosure. The set of data can include a plurality of events 540. Each event in the plurality of events 540 can be correlated with a time in a plurality of times 512 and a meaning in a plurality of meanings 510. A row of events can be analyzed to determine a set of functions 530 corresponding to each of the plurality of meanings 510 (this can be as provided for with respect to FIGS. 4A-4C). The plurality of events 540 can be analyzed as a collective function 550.

The matrix shown in FIG. 5A is the collection of all the associated times with the events they designate. Normality can be calculated and even long term trends that are undetectable otherwise, can become apparent. The interaction of events becomes detectable; where (for example) the relationship between Fred's potential tardiness or inebriation versus the profit and loss of a hedge fund is defined as a dependency when their routines are compared. Or more generally, everyone's routines are interdependent in ways that are unknown today.

The present disclosure can provide for collecting the ordered pairs of time and result—that is the temporal metric. These ordered pairs can be represented as F(T), where any one answer is F (t0). The present disclosure can then provide for creating a collection of F (tn) where n corresponds to the same time on different days. The present disclosure can then provide for analyzing the collection to determine trends that can indicate an underlying health issue. These collections can be created for several different metrics, for example, foot stride as a first metric and heart rate as a second metric. Then the trends from each metric can be analyzed in concert to determine if the cross correlation indicate any underlying health issue.

The collection of metrics can be auto-correlated at discrete times. The metrics will be cross-correlated at corresponding discrete times. The auto and cross correlation can be analyzed to determine underlying health trends.

In one examples of the present disclosure, f(t) can the foot position at the time the foot moves. f(deltaT) can be the stride. F(T) can be the stride function over time. The stride function over time at an instance provides the stride metric for that instance. g(t) can be the heart beat at the time the heart beats. g(deltaT) can be the heart rate. G(T) can be the heart rate function over time. The heart rate function over time at an instance provides the heart rate metric for that instance.

Therefore, FIG. 5A shows how the events in a routine can be organized, time stamped, measured as a single record of a routine a collection of F (tn) where F (tn) is a routine result at a specific time. For example, in 550, {Fk (tn)|K=1, 30000; n=0,N}.

Figure 5B:
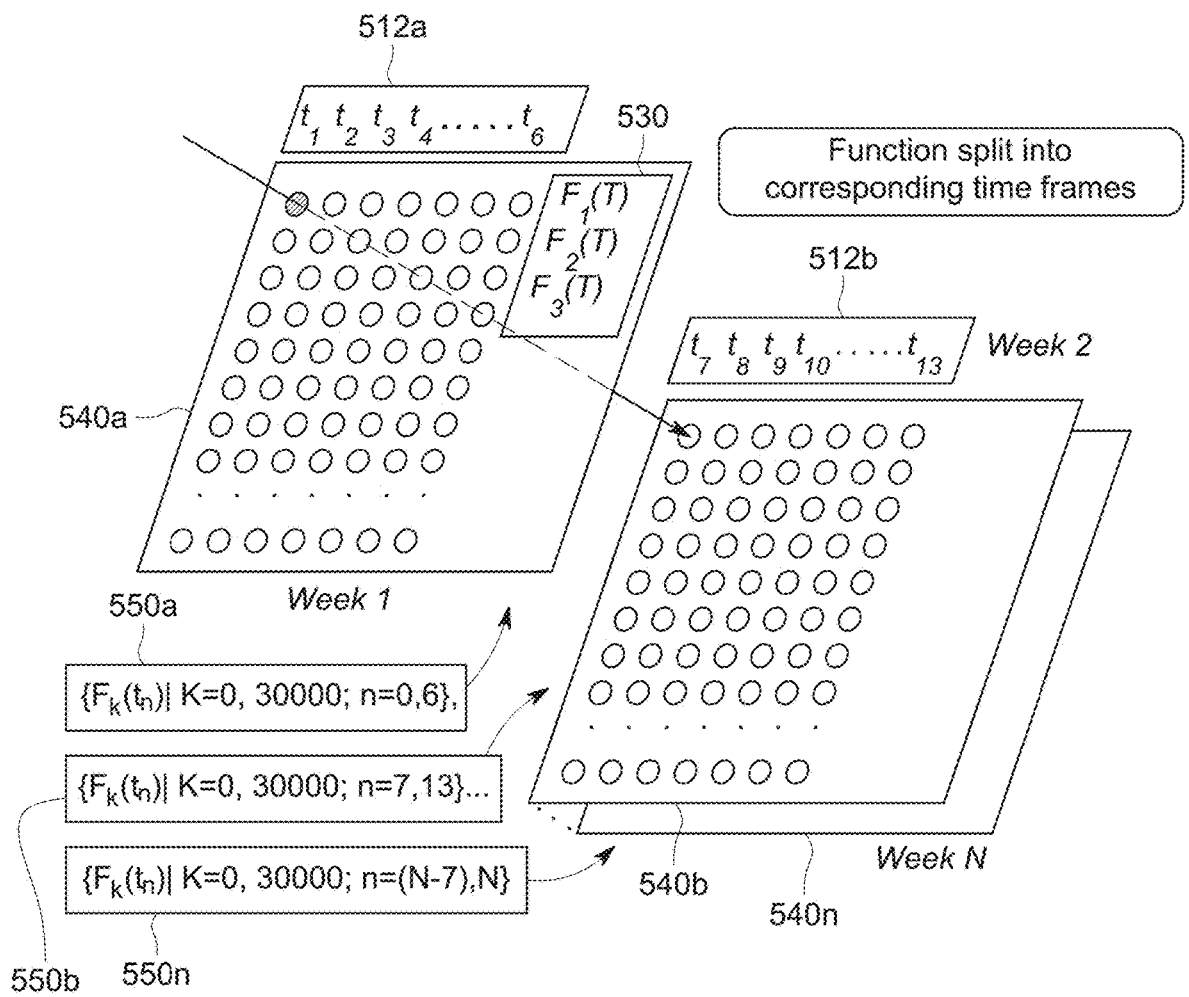
FIG. 5B shows exemplary data sets capturing the same data over different periods of time, according to an embodiment of the present disclosure.

FIG. 5B shows exemplary data sets capturing the same data over different periods of time, according to an embodiment of the present disclosure. Each of the elements of FIG. 5B can be as provided for with respect to similarly labeled elements of FIG. 5A. A first set of events 540a can be correlated with a first set of times 512a and a first collective function 550a. A second set of events 540b can be correlated with a second set of times 512b and a second collective function 550b. An nth set of events 540n can be correlated with an nth set of times 512n and an nth collective function 550n.

Figure 6:
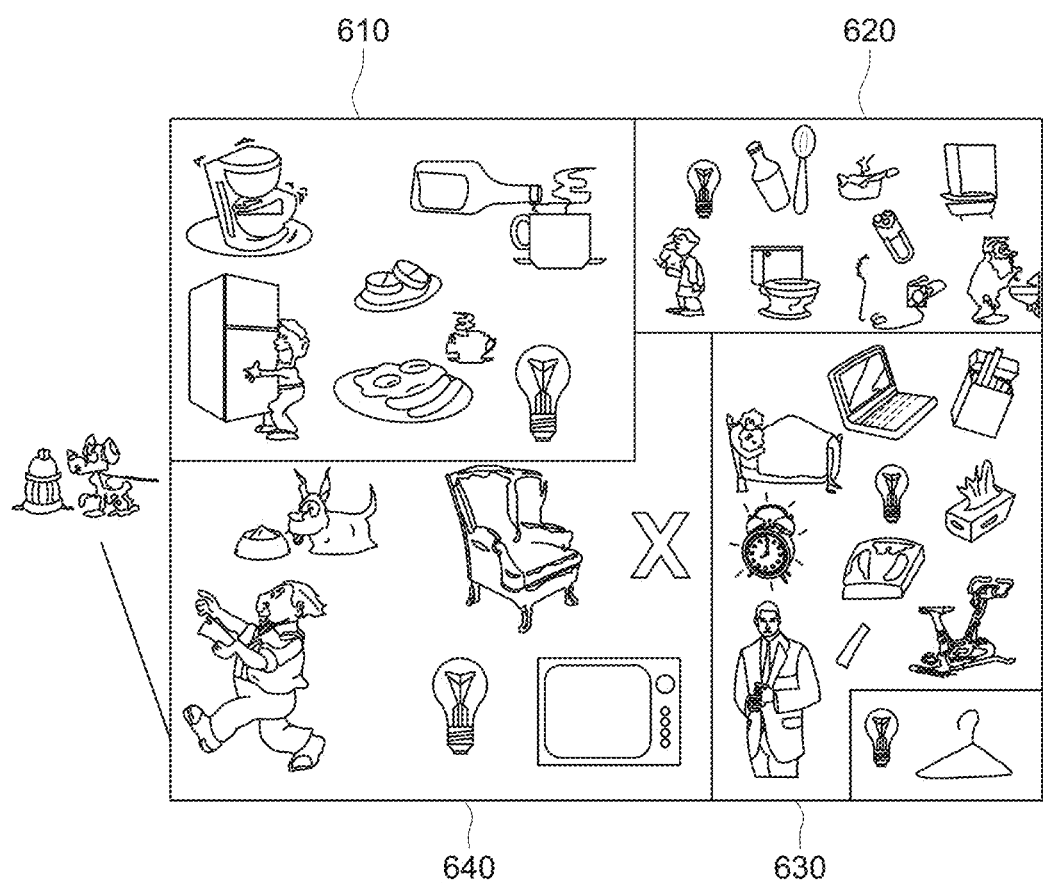
FIG. 6 shows exemplary sets of events which can be correlated, according to an embodiment of the present disclosure.

FIG. 6 shows exemplary sets of events 610, 620, 630, and 640 which can be correlated, according to an embodiment of the present disclosure. Each of the events can be correlated with a particular room in a house. For example, events 610 can be in the kitchen, events 620 in the bathroom, events 630 in the bedroom, and events 640 in a common room. Each event can be detected by a plurality of sensors configured to detect the status of the event, as provided for above with respect to FIG. 2. For example, there can be sensors in the containers, toothbrush, ashtray and the coffee machine. The lights can indicate when they are turned off and on. A user's routine can be completely monitored as an indication of continuous activity and wellness. The fully instrumented abode can have a wellness and perimeter security connected at point X.

Figure 7:
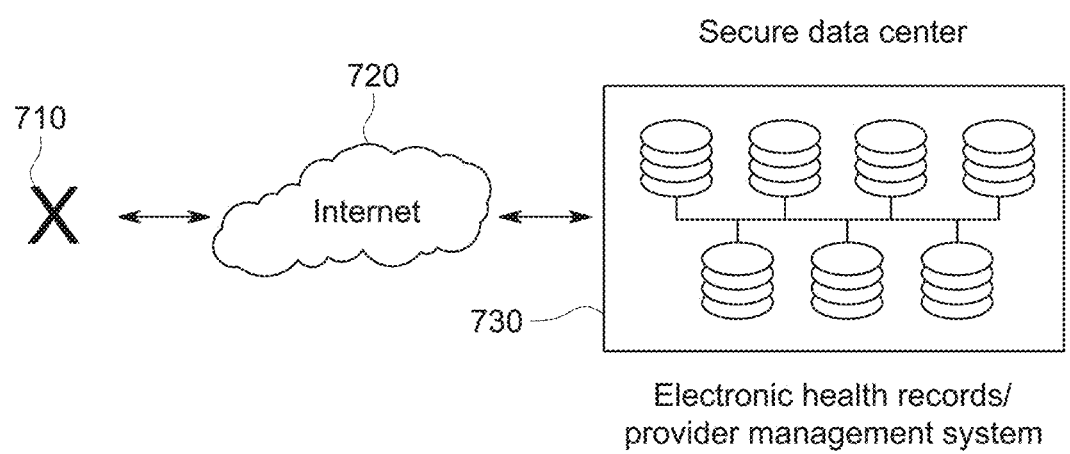
FIG. 7 shows an exemplary system for collecting and storying data, according to an embodiment of the present disclosure.

FIG. 7 shows an exemplary system 700 for collecting and storying data, according to an embodiment of the present disclosure. The system 700 can include a user's sensor system 710; an online network 720; and a secure data center 730. Sensors in the user's sensor system 710 can be configured to send their data via the online network 720 to the secure data center 730. The data can be analyzed in the secure data center 730 according to the various embodiments of the present disclosure.

Some examples of the present disclosure can be administered locally. In other examples, a remote processing/database 730 can be provided. The remote system 730 can be a HIPPA certified "EHR" environment connected by end to end encryption from the sensors 710 to the data center.

Such a system 700 can provide the ability to contain and integrate HIPPA complaint data from the individual's medical records for a more complete analysis of wellness. Additionally, such a system 700 can require much maintenance and computing power; an offsite database 730 can provide uninterrupted power and off-site backup of all data. Complexity can be centralized for ease of software and hardware maintenance. Furthermore, a remote data center 730 can provide increased data storage for the vast amount of sensor data and computing correlations. The remote data center 730 can monitor and determine when to contact the user or a caregiver for the user. Lastly, a remote system 730 can provide a HIPPA compliant environment to securely store the routine data with the individual's medical records under a legally controlled encrypted data envelope.

Therefore, the present disclosure provides a type of monitoring ideal for assisted living centers, senior communities, nursing homes, and all those who live alone. A normal resident can be converted to an embodiment of the present disclosure with the purchase of everyday items configured or modified with encrypting Wi-Fi sensors to detect their use and potentially collect more sophisticated data. Indeed, a failing device can not only signal its need for replacement—it can order the replacement as well.

Further, monitoring the MIRP data can be far less expensive and intrusive than monitoring vitals. The present disclosure can also provide for monitoring the activity/wellness of any spontaneous entity, including animals, livestock, and automated equipment. For example, monitoring the wellness of a subway system, in this manner, could reveal interaction with numerous incidental events, such as a taxi strike, a popular Broadway show, visiting dignitaries, or the tardiness and/or alertness of employees.

FIG. 8A, and FIG. 8B illustrate exemplary possible system configurations. The more appropriate configuration will be apparent to those of ordinary skill in the art when practicing the present technology. Persons of ordinary skill in the art will also readily appreciate that other system configurations are possible.

FIG. 8A illustrates a conventional system bus computing system architecture 800 wherein the components of the system are in electrical communication with each other using a bus 805. Exemplary system 800 includes a processing unit (CPU or processor) 810 and a system bus 805 that couples various system components including the system memory 815, such as read only memory (ROM) 820 and random access memory (RAM) 825, to the processor 810. The system 800 can include a cache of high-speed memory connected directly with, in close proximity to, or integrated as part of the processor 810. The system 800 can copy data from the memory 815 and/or the storage device 830 to the cache 812 for quick access by the processor 810. In this way, the cache can provide a performance boost that avoids processor 810 delays while waiting for data. These and other modules can control or be configured to control the processor 810 to perform various actions. Other system memory 815 can be available for use as well. The memory 815 can include multiple different types of memory with different performance characteristics. The processor 810 can include any general purpose processor and a hardware module or software module, such as module 1 832, module 2 834, and module 3 836 stored in storage device 830, configured to control the processor 810 as well as a special-purpose processor where software instructions are incorporated into the actual processor design. The processor 810 can essentially be a completely self-contained computing system, containing multiple cores or processors, a bus, memory controller, cache, etc. A multi-core processor can be symmetric or asymmetric.

To enable user interaction with the computing device 800, an input device 845 can represent any number of input mechanisms, such as a microphone for speech, a touch-sensitive screen for gesture or graphical input, keyboard, mouse, motion input, speech and so forth. An output device 835 can also be one or more of a number of output mechanisms known to those of skill in the art. In some instances, multimodal systems can enable a user to provide multiple types of input to communicate with the computing device 800. The communications interface 840 can generally govern and manage the user input and system output. There is no restriction on operating on any particular hardware arrangement and therefore the basic features here can easily be substituted for improved hardware or firmware arrangements as they are developed.

Storage device 830 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 825, read only memory (ROM) 820, and hybrids thereof.

The storage device 830 can include software modules 832, 834, 836 for controlling the processor 810. Other hardware or software modules are contemplated. The storage device 830 can be connected to the system bus 805. In one aspect, a hardware module that performs a particular function can include the software component stored in a computer-readable medium in connection with the necessary hardware components, such as the processor 810, bus 805, display 835, and so forth, to carry out the function.

FIG. 8B illustrates a computer system 850 having a chipset architecture that can be used in executing the described method and generating and displaying a graphical user interface (GUI). Computer system 850 is an example of computer hardware, software, and firmware that can be used to implement the disclosed technology. System 850 can include a processor 855, representative of any number of physically and/or logically distinct resources capable of executing software, firmware, and hardware configured to perform identified computations. Processor 855 can communicate with a chipset 860 that can control input to and output from processor 855. In this example, chipset 860 outputs information to output 865, such as a display, and can read and write information to storage device 870, which can include magnetic media, and solid state media, for example. Chipset 860 can also read data from and write data to RAM 875. A bridge 880 for interfacing with a variety of user interface components 885 can be provided for interfacing with chipset 860. Such user interface components 885 can include a keyboard, a microphone, touch detection and processing circuitry, a pointing device, such as a mouse, and so on. In general, inputs to system 850 can come from any of a variety of sources, machine generated and/or human generated.

Chipset 860 can also interface with one or more communication interfaces 890 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 855 analyzing data stored in storage 870 or 875. Further, the machine can receive inputs from a user via user interface components 885 and execute appropriate functions, such as browsing functions by interpreting these inputs using processor 855.

It can be appreciated that exemplary systems 800 and 850 can have more than one processor 810 or be part of a group or cluster of computing devices networked together to provide greater processing capability.

Additional Embodiments

The present disclosure provides systems which can detect subtle signs that an individual is somehow diminished in routine performance, even before the individual notices or accepts, or who may even discount it. Issues can include that the individual is sleeping longer, is not as alert, has not recovered from an illness as quickly, has less stamina, is eating poorly, or even smells sick.

The present disclosure can therefore detect signs of depression, which can be as deadly as smoking or obesity in people who become isolated. As more and more people are shut in, and often alone with only a Google Home or Amazon Echo as their substitute partner, this is an attempt to automate the observance of that diminished routine performance and stimulate an intervention.

The mathematical reduction of the trend shown can be only one of several algorithms to detect something abnormal. Some embodiments of the present disclosure can provide comparisons to other individuals, analysis of historical patterns, or analysis of preceding events. Indeed, a profile of routine behavior for a given person can also categorize them for being at risk requiring intervention. Other qualified individuals, recognized in the area, can even be alerted to intervene based on a trigger of a serious aberration (e.g. like a stumbling wobbly walk).

In one embodiment of the present disclosure, an automated sense of smell can act as a means to detect certain illnesses in the future.

Overall, sensor systems according to the present disclosure can be passive and not require the active participation of the observed.

In some examples, cameras can analyze the pace and spring in someone's gait from such videos.

One embodiment of the present disclosure can provide for a simple interrogatory with the user to ask specific questions relating to depression, or to address additional symptoms of a malady that fit the deviation in routine.

For clarity of explanation, in some instances the present technology can be presented as including individual functional blocks including functional blocks comprising devices, device components, steps or routines in a method embodied in software, or combinations of hardware and software.

In some configurations the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general-purpose computer, special purpose computer, or special purpose processing device to perform a certain function or group of functions. Portions of computer resources used can be accessible over a network. The computer executable instructions can be, for example, binaries, intermediate format instructions such as assembly language, firmware, or source code. Examples of computer-readable media that can be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

While various examples of the present invention have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:
1. A method comprising:
receiving, via a first plurality of sensors, first activity data associated with a first individual and a first plurality of events, wherein the first plurality of events occur in a first order over a first time period;

based at least in part on the first activity data and the first plurality of events, determining a first routine associated with the first individual;

receiving, via a second plurality of sensors, second activity data associated with a second individual and a second plurality of events, wherein the second plurality of events occur in a second order over a second time period;

based at least in part on the second activity data and the second plurality of events, determining a second routine associated with the second individual;

subsequent to the determining the first routine, receiving, via the first plurality of sensors, third activity data associated with the first individual and a third plurality of events, wherein the third plurality of events occur in a third order over a third time period;

based at least in part on the third activity data and the first routine, identifying a first deviation from the first routine;

subsequent to the determining the second routine, receiving, via the second plurality of sensors, fourth activity data associated with the second individual and a fourth plurality of events, wherein the fourth plurality of events occur in a fourth order over a fourth time period;

based at least in part on the fourth activity data and the second routine, identifying a second deviation from the second routine;

determining, based at least in part on the first deviation and the second deviation, a permissible deviation;

receiving, via the first plurality of sensors, fifth activity data associated with the first individual and a fifth plurality of events, wherein the fifth plurality of events occur in a fifth order over a fifth time period; and based at least in part on the fifth activity data, the permissible deviation, and the first routine, identifying a third deviation from the first routine, the third deviation being an abnormal deviation from the first routine.

2. The method of claim 1, wherein the first time period is a day, each event in the first plurality of events occurring once in the first time period and the second time period is a day, each event in the second plurality of events occurring once in the second time period.

3. The method of claim 1, further comprising in response to identifying the third deviation, transmitting a notification indicating the presence of the third deviation.

4. The method of claim 1, wherein the third deviation is based at least in part on a magnitude of a difference between the first order and the fifth order.

5. The method of claim 1, wherein the third plurality of events includes at least a portion of the events included in the first plurality of events and the fourth plurality of events includes at least a portion of the events included in the second plurality of events.

6. The method of claim 5, wherein fifth plurality of events includes at least a portion of the events included in the first plurality of events.

7. The method of claim 5, wherein the first deviation is determined based on a first one of the third plurality of events occurring at a different time compared to a first one of the first plurality of events, wherein the first one of the third plurality of events and the first one of the first plurality of events correspond to the same event, and the second deviation is determined based on a first one of the fourth plurality of events occurring at a different time compared to a first one of the second plurality of events, wherein the first one of the fourth plurality of events and the first one of the second plurality of events correspond to the same event.

8. The method of claim 1, wherein the third order is the same as the first order and the fourth order is the same as the second order.

9. The method of claim 8, wherein fifth order is the same as the first order.

10. The method of claim 1, wherein the first deviation is determined based on the third order being different than the first order and the second deviation is determined based on the fourth order being different than the second order.

11. The method of claim 1, wherein determining the first routine comprises:

detecting a first timing and a first completion indicator of each event in the first plurality of events;

based on the first detected timing and the first completion indicator of each event in the first plurality of events, determining first correlations between a portion of events in the first plurality of events;

determining a first plurality of time windows corresponding to the first plurality of events, wherein each time window in the first plurality of time windows indicates when the corresponding event in the first plurality of events occurs during the first time period; and determining the first routine based on the determined first correlations and the determined first plurality of time windows.

12. The method of claim 11, wherein determining the second routine comprises:

detecting a second timing and a second completion indicator of each event in the second plurality of events;

based on the second detected timing and the second completion indicator of each event in the second plurality of events, determining second correlations between a portion of events in the second plurality of events;

determining a second plurality of time windows corresponding to the second plurality of events, wherein each time window in the second plurality of time windows indicates when the corresponding event in the second plurality of events occurs during the second time period; and determining the second routine based on the determined second correlations and the determined second plurality of time windows.

13. The method of claim 12, wherein the identifying the third deviation includes determining whether at least one event in the fifth plurality of events occurred outside of the first determined window for the at least one event in the first plurality of events, wherein the fifth plurality of events include the same events as the first plurality of events.

14. The method of claim 12, wherein the identifying the third deviation further includes:

determining a wellness metric based on the first activity data, the third activity data, the fifth activity data, and the first routine; and determining that the determined wellness metric is below a threshold.

15. The method of claim 1, wherein the first plurality of sensors and the second plurality of sensors include wearable sensors.

16. A non-transitory computer-readable medium, in which is embedded computer-readable code, that, when loaded on a computer, causes the computer to perform the steps of:

receiving, via a first plurality of sensors, first activity data associated with a first individual and a first plurality of events, wherein the first plurality of events occur in a first order over a first time period;

based at least in part on the first activity data and the first plurality of events, determining a first routine associated with the first individual;

receiving, via a second plurality of sensors, second activity data associated with a second individual and a second plurality of events, wherein the second plurality of events occur in a second order over a second time period;

based at least in part on the second activity data and the second plurality of events, determining a second routine associated with the second individual;

subsequent to the determining the first routine, receiving, via the first plurality of sensors, third activity data associated with the first individual and a third plurality of events, wherein the third plurality of events occur in a third order over a third time period;

based at least in part on the third activity data and the first routine, identifying a first deviation from the first routine;

subsequent to the determining the second routine, receiving, via the second plurality of sensors, fourth activity data associated with the second individual and a fourth plurality of events, wherein the fourth plurality of events occur in a fourth order over a fourth time period;

based at least in part on the fourth activity data and the second routine, identifying a second deviation from the second routine;

determining, based at least in part on the first deviation and the second deviation, a permissible deviation;

receiving, via the first plurality of sensors, fifth activity data associated with the first individual and a fifth plurality of events, wherein the fifth plurality of events occur in a fifth order over a fifth time period; and based at least in part on the fifth activity data, the permissible deviation, and the first routine, identifying a third deviation from the first routine, the third deviation being an abnormal deviation from the first routine.

17. The non-transitory computer-readable medium of claim 16, further comprising in response to identifying the third deviation, transmitting a notification indicating the presence of the third deviation.

18. The non-transitory computer-readable medium of claim 16, wherein the third deviation is based on a magnitude of a difference between the first order and the fifth order.

19. A system, comprising:
a first plurality of sensors and a second plurality of sensors;
a first processor communicatively coupled to the first plurality of sensors and a second processor communicatively coupled to the second plurality of sensors;
a memory having stored therein a plurality of code sections executable by the first and second processors, the plurality of code comprising instructions for:
receiving, via the first plurality of sensors, first activity data associated with a first individual and a first plurality of events, wherein the first plurality of events occur in a first order over a first time period;
based at least in part on the first activity data and the first plurality of events, determining a first routine associated with the first individual;
receiving, via the second plurality of sensors, second activity data associated with a second individual and a second plurality of events, wherein the second plurality of events occur in a second order over a second time period;
based at least in part on the second activity data and the second plurality of events, determining a second routine associated with the second individual;
subsequent to the determining the first routine, receiving, via the first plurality of sensors, third activity data associated with the first individual and a third plurality of events, wherein the third plurality of events occur in a third order over a third time period;
based at least in part on the third activity data and the first routine, identifying a first deviation from the first routine;
subsequent to the determining the second routine, receiving, via the second plurality of sensors, fourth activity data associated with the second individual and a fourth plurality of events, wherein the fourth plurality of events occur in a fourth order over a fourth time period;
based at least in part on the fourth activity data and the second routine, identifying a second deviation from the second routine;
determining, based at least in part on the first deviation and the second deviation, a permissible deviation;
receiving, via the first plurality of sensors, fifth activity data associated with the first individual and a fifth plurality of events, wherein the fifth plurality of events occur in a fifth order over a fifth time period; and
based at least in part on the fifth activity data, the permissible deviation, and the first routine, identifying a third deviation from the first routine, the third deviation being an abnormal deviation from the first routine.

20. The system of claim 19, wherein the third deviation is based on a magnitude of a difference between the first order and the fifth order.

* * * * *